United States Patent [19]

Waitman

[11] Patent Number: 5,369,365
[45] Date of Patent: Nov. 29, 1994

[54] COMBINED WATER FIELD STRENGTH AND CONDUCTIVITY METER

[76] Inventor: David B. Waitman, 5309 Hawthorne Rd., Chubbuck, Id. 83202

[21] Appl. No.: 567,592

[22] Filed: Aug. 15, 1990

Related U.S. Application Data

[63] Continuation-in-part of Ser. No. 347,447, May 4, 1989, abandoned.

[51] Int. Cl.⁵ ............... G01N 27/02; A01K 61/00
[52] U.S. Cl. ............................. 324/444; 324/439
[58] Field of Search ............ 324/439, 444, 457, 365, 324/425, 72, 450; 119/3

[56] References Cited

U.S. PATENT DOCUMENTS

| | | | |
|---|---|---|---|
| 2,778,140 | 2/1957 | Applegate et al. | 119/3 |
| 3,487,301 | 12/1969 | Gardner et al. | 324/64 |
| 3,566,233 | 2/1971 | Kahn | 324/71.1 |
| 4,070,616 | 1/1978 | Kristinsson | 324/693 |
| 4,209,741 | 6/1986 | Coby et al. | 324/64 |
| 4,593,648 | 6/1986 | Marzluf | 119/3 |
| 4,808,931 | 2/1989 | Ling | 324/444 |
| 4,918,391 | 4/1990 | Byrd | 324/439 |

FOREIGN PATENT DOCUMENTS 1553252 3/1975 United Kingdom ............... 324/439

*Primary Examiner*—Maura K. Regan
*Attorney, Agent, or Firm*—Hopkins, Roden, Crockett, Hansen & Hoopes

[57] ABSTRACT

A combined water field strength and conductivity meter. The meter is intended for use with a separate electroshocker for use in a body of water to produce electrotaxis in fish in order to collect the fish. The meter includes a conductivity probe which is placed within the water. Pairs of electrodes within the probe detect water conductivity and the voltage potential produced by the electroshocker. A processing unit applies and measures a known current between the first pair of electrode and measures the voltage potential between the second pair of electrodes. An LCD display connected to the processing unit displays the results so that the electroshocker may be optimally adjusted.

20 Claims, 4 Drawing Sheets

COMBINED WATER FIELD STRENGTH AND CONDUCTIVITY METER

FIELD OF THE INVENTION

This application is a continuation-in-part of patent application Ser. No. 07/347,447 filed May 4, 1989, now abandoned.

This invention relates to testing equipment and, more particularly, to an apparatus for measuring the conductivity of a body of water and for measuring a voltage gradient within the same body of water. An electric field can then be applied to the water for inducing electrotaxis in fish so as to enable their capture for study.

BACKGROUND OF THE INVENTION

Electrotaxis as used herein means the involuntary movement of fish in an electric field toward the positive electrode. This condition is often utilized in research and resource management to inventory, inspect, and mark fish. Assuming the electric field has been properly regulated for the given body of water, in order to initiate electrotaxis, sufficient voltage must be available in the water adjacent the positive electrode to momentarily stun the fish and enable researchers to gather them with nets or the like. At the same time, however, the voltage must not be so great as to permanently harm the fish.

Different bodies of water may have markedly different abilities to conduct electricity therethrough, and indeed the same body of water may exhibit significant differences in conductivity in different locals. For instance, a relatively clean portion of a fresh-water lake, such as in the center of the lake least subject to contamination by runoff may be quite clean and offer significant resistance to an electric current induced therein. However, in the portion of the same freshwater lake subject to contamination by a mineral spring, creek or river, quite high conductivities may be experienced. Likewise, temperature variation in a body of water can dramatically alter the conductivity. For instance, the resistance of cold tap water (about 50° F.) is on the order of 3,000 ohms, while the resistance of the same water warmed to about 68° F. decreases to about 1,500 ohms.

Fisheries' biologists have a need to ascertain fish population data through methods which permit recovery of a significant percentage of fish, without permanently damaging the fish. "Electrofishing" has become the method of choice for such fish collecting as it is relatively easy and effective. However, a significant problem exists in the proper application of the electric field to the body of water so as to apply the optimum current to collect the maximum number of fish for analysis without damaging or killing any of such fish. Heretofore, operators of the electrofishing equipment have had no means to test a given body of water within which electrofishing was to take place. They simply applied a voltage field to the body of water and presumed it would be strong enough to induce electrotaxis but not so strong as to damage fish.

Conductivity meters have long been available for laboratory use. In general, such meters do not provide an actual conductivity reading, but rather a standard conductivity reading which is corrected to 25° C. With reference to a standardized chart, an indication of the relative conductivity of the particular water tested is obtained. Experience indicated that the initial voltage applied in the field was often incorrect and either no electrotaxis occurred, or fish were killed or damaged due to the application of excessive voltage to the body of water.

The conductivity of potable waters in the United States generally ranges from about 20 to about 1,500 micromhos/cm. Exceedingly clean water exhibits very low conductivity, and higher voltages or an increase in the size of electrodes utilized, is, therefore, required in order to generate electrotaxis in fish. Maintaining a large cathode (boat hull) to anode ratio (10:1 minimum) permits the cathode to distribute the field over a larger area, and by electrotaxis, cause the fish to approach the anode. In waters of very low conductivity (less than 200 micromhos/cm) very high voltages must be used. If the biologists utilizing such voltages are moving through a body of water, and unknowingly enter a higher conductivity area, the high voltages used may kill many fish.

Therefore, it is an object of this invention to provide a portable hand-held apparatus which may be utilized to not only determine the conductivity of a localized area within a body of water, but which may also measure the field strength of the voltage applied to such water to ensure that a shocking voltage is within an optimum range. Such apparatus is provided with electronics enabling it to readily switch from measuring conductivity to measuring field strength, thereby providing operators of the voltage source with immediate information enabling more precise operation.

It is a further object of the present invention to provide a method for accurately measuring the actual conductivity of a body of water so that an optimum voltage electric field may be applied to the water, with the electric field being measured by the same apparatus, and the conductivity or field strength displayed.

These and other objects of the invention will become readily apparent with reference to the following description and claims.

SUMMARY OF THE INVENTION

The present invention provides a portable hand-held apparatus for measuring the actual conductivity of a given body of water and for measuring the strength of an electric field applied to the body of water. This data can then be used in combination with an electroshocker to apply a voltage to the water in order to induce electrotaxis in fish to be collected for research purposes. The portable hand-held apparatus of the invention is intended for use with a separate electroshocker apparatus and generally stated comprises:

- a conductivity probe formed to permit water flow therethrough;
- a first pair of electrodes mounted within the conductivity probe for measuring a known current applied to the water to indicate the conductivity of the water;
- a second pair of electrodes mounted within the conductivity probe for measuring a voltage potential caused by the electroshocker;
- processing means electrically connected to the first and second pairs of electrodes for applying a known current to the first pair of electrodes in order to measure water conductivity and for measuring a voltage potential between the second pair of electrodes; and
- display means electrically connected to the processing means for displaying data from the processing means.

In the use of an electroshocker, it is important to reasonably accurately determine the conductivity of the body of water prior to introducing an electric field therein. If the conductivity is substantially different than that anticipated when the electric field is introduced, the fish will either be scared away by the mild electric field or may be killed if too great a voltage is applied to the water. The apparatus of the present invention is thus adapted to permit a researcher to not only measure conductivity of a given body of water, but also measure the strength of a field of electricity applied to such body of water by the electroshocker. Both measurements may be made by the apparatus of the invention easily and quickly. A visual readout of conductivity is also provided. This readout can then be used for applying a suitable electric field to the water utilizing the electroshocker which shocks the fish to the surface for collection.

In the use of the separate electroshocker, the probe of the invention can be returned to the water as required to measure the strength of the voltage being applied. This voltage as required to obtain an optimal voltage setting. Other objects, advantages, and capabilities of the present invention will become more apparent as the description proceeds.

DETAILED DESCRIPTION OF THE INVENTION

Figure 1:
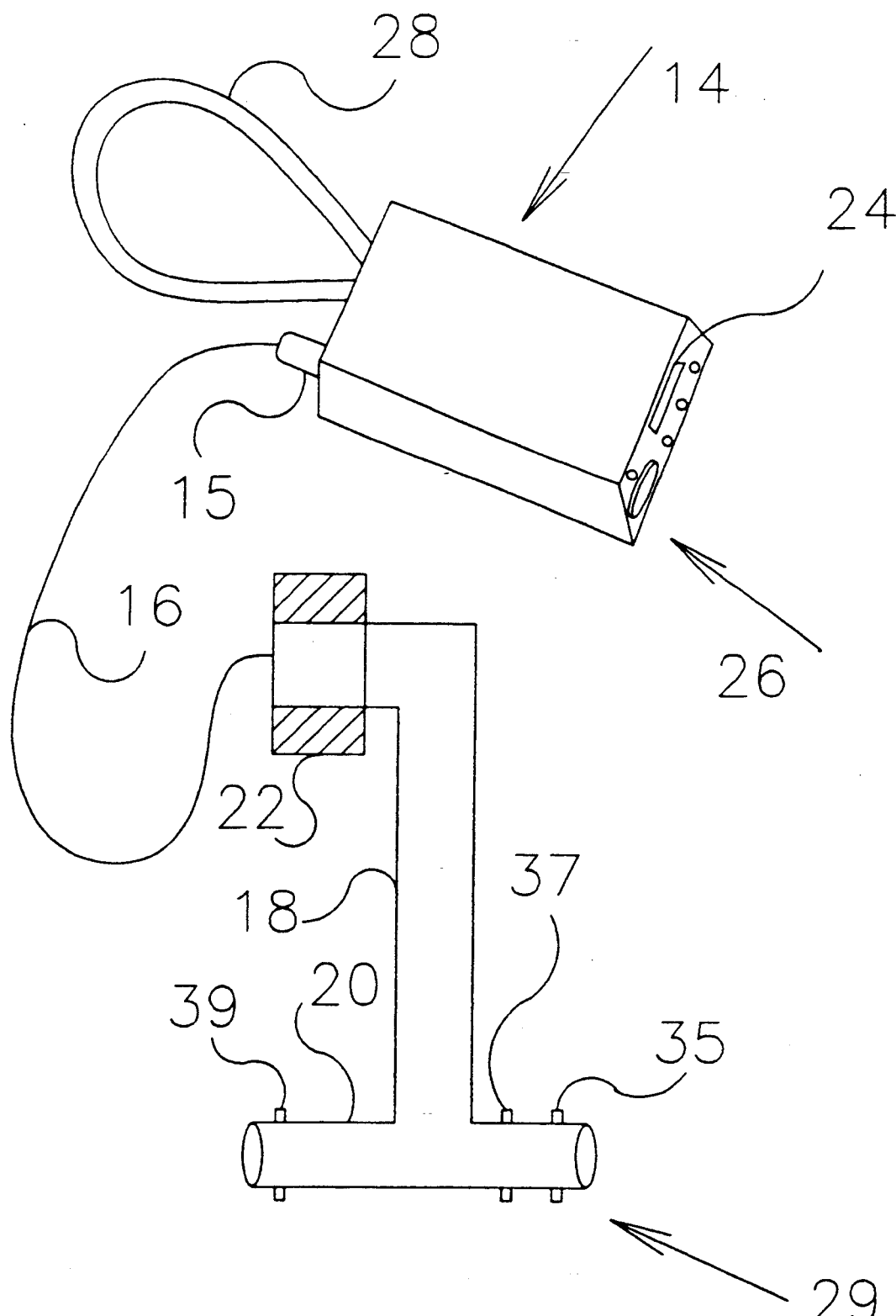
FIG. 1 is a schematic representation of a portable field-strength and conductivity meter constructed in accordance with the invention.

Referring now to FIG. 1, the combined water field-strength and conductivity meter is shown and generally comprises:

- a conductivity probe 12 formed to permit water flow therethrough;
- a first pair of electrodes (35,37) mounted within the conductivity probe for measuring a known current applied to the water to indicate the conductivity of the water;
- a second pair of electrodes (37,39) mounted within the conductivity probe for measuring a voltage potential caused by the electroshocker;
- processing means 14 for applying a known current to the first pair of electrodes (35,37) to measure water conductivity and for measuring a voltage potential between the second pair of electrodes (37,39); and
- display means 24 for displaying data from the processing means 14.

As shown in FIG. 1, the conductivity probe 12 and processing means 14 are electrically interconnected by a cable 16. The field strength conductivity probe 12 is generally T-shaped and comprises an elongate tube portion 18 and a shorter sampling portion 20. The length of tube portion 18 may be varied depending upon the depth of the water being analyzed. Separate conductivity probes 12 of varying lengths may be disconnected from the data processing unit 14 and interchanged depending upon the particular requirements by connection means in the form of a connector 15. A handle 22 may be provided on the conductivity probate 12 and a hand strap 28 may also be provided on the processing unit 14.

The data processing unit 14 includes the display means 24 for displaying alpha-numeric data as well as various control knobs 26 for adjusting electronic circuitry therein.

Figure 2:
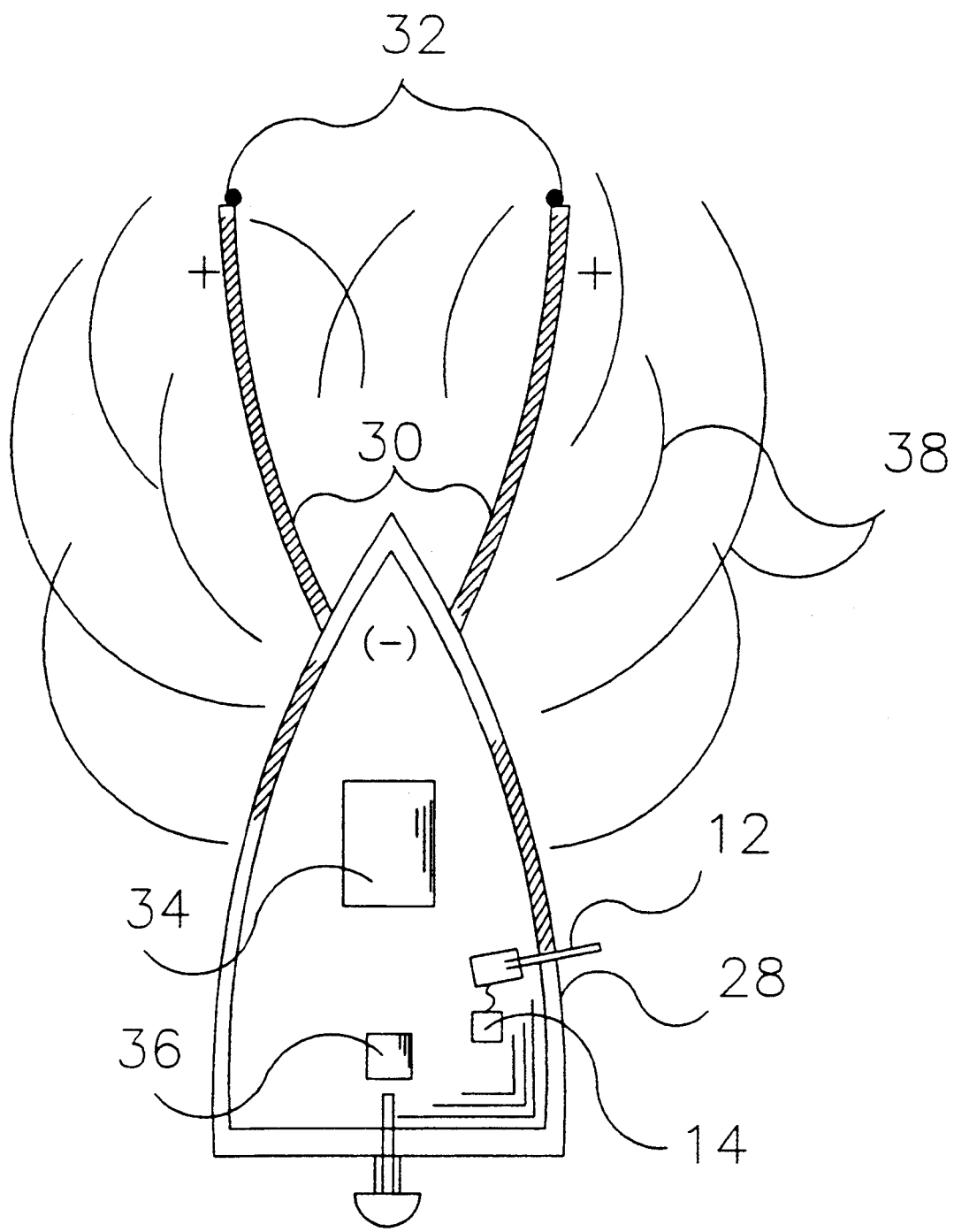
FIG. 2 is a schematic representation of the meter of the invention as used in conjunction with a separate electroshocker.

The apparatus of the present invention is intended for use in conjunction with an electroshocking apparatus, commonly known to those skilled in this art. By way of example and with reference to FIG. 2, a metal boat 28 may be provided with a pair of booms 30 each having an electrode 32 at its distal end immersed in the water. In the embodiment of FIG. 2, the electrodes 32 comprise anodes while the metal boat 28 comprises the cathode. An ungrounded generator 34 is provided to generate up to 5 kilowatts of either 120- or 220-volt alternating current. An electroshocker 36 rectifies the AC current to pulsating DC current and directs such current to the anodes 32 at the end of booms 30. Electroshocking devices such as those manufactured by Coeffelt Electronics Company of Englewood, Colorado or Smith-Root Company of Vancouver, Wash. may be utilized. The electric field 38 is distributed between the electrodes 28, 32. The current density and voltage gradient, however, are highest near the electrodes and most of the voltage is distributed in this region.

Figure 3A:
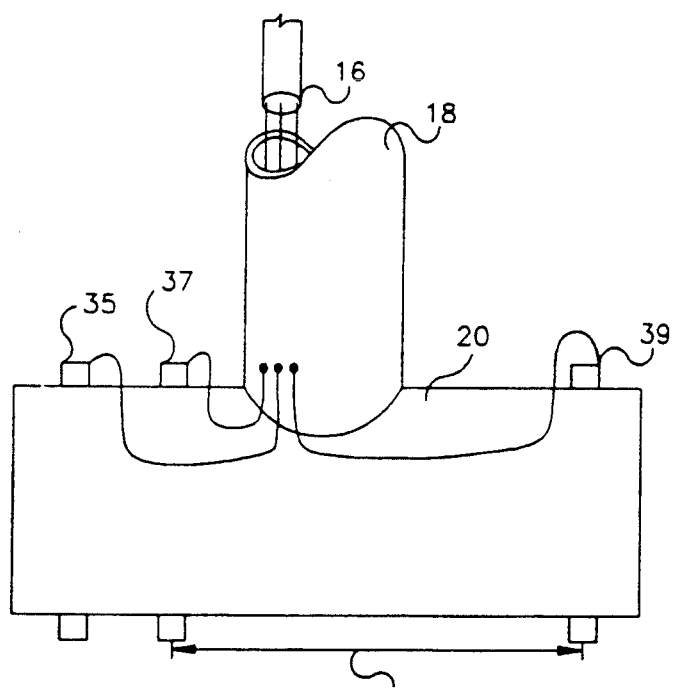
FIG. 3A is a partial side elevation view of a conductivity probe of the meter of the invention.
Figure 3B:
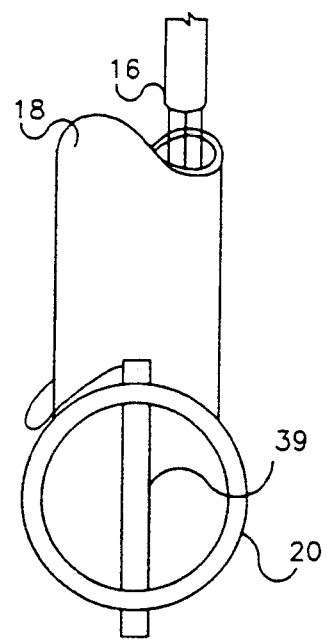
FIG. 3B is an end view of FIG. 3A.

FIGS. 3A and 3B illustrate in more detail the sampling portion 20 of the conductivity. As previously stated, first electrode pair (35,37) and second electrode pair (37,39) are mounted within the sampling portion 20. Middle electrode 37 is common to both pairs of electrodes (35,37) and (37,39). The three electrodes 35, 37, and 39 are in the form of metal pins inserted through the tubular plastic sampling portion 20.

The electrode pairs (35,37 and 37,39) contained within the probe 20 may be variously configured. In the illustrative embodiment of the invention, three electrodes are utilized: the first pair (35,37) functions to measure conductivity, the second pair (37,39) functions to measure field strength, the arrangement's common electrode 37 functions as a cathode, and the electrode 39 as an anode. Alternatively, two separate pairs of distinct electrodes may be provided, one for each function. It is to be understood that if a probe having only one function is desired, only a single set of electrodes is necessary.

Figure 4:
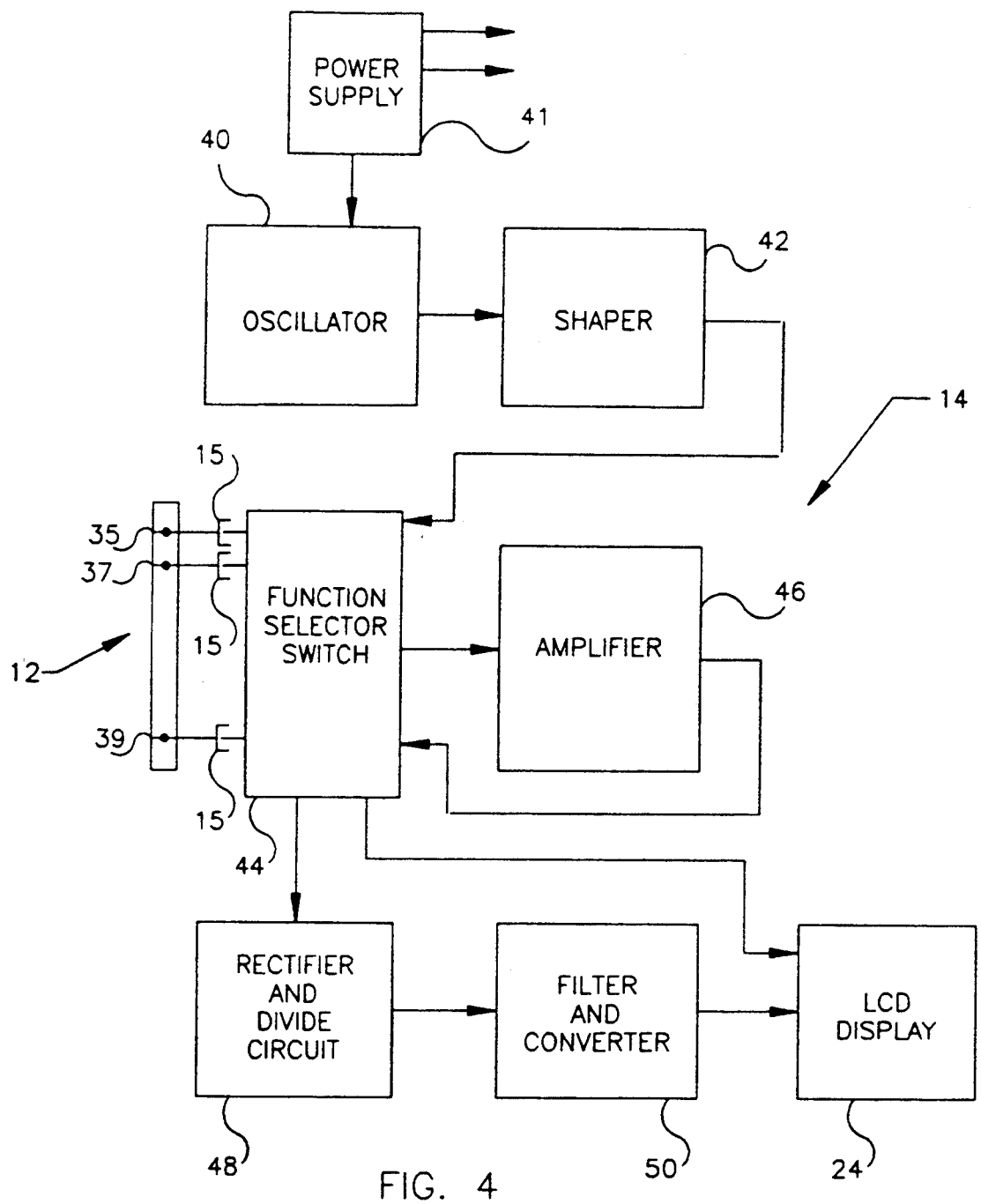
FIG. 4 is a schematic block diagram showing electronic components of a processing means of the invention.

With reference to FIG. 4, the processing means 14 of the invention is shown. The processing means includes a power supply 41 such as 9-volt nicad batteries or the like. The processing means 14 also includes a 1-kilohertz oscillator 40 for generating sine waves. A wave shaper 42 connected to the oscillator 40 clips the waves to about 0.7 volts. The waves are clipped to minimize electrolysis in the water immediately adjacent the pair of electrodes (35,37), which adversely effects conductivity readings. The clipped sine wave of known current value is directed to a function selector switch 44. The function selector 44 routes the wave via 3-pin connector 15, to electrode 35 disposed within the sampling portion 20 of conductivity probe 12. Common electrode 37 within the sampling portion 20 receives the known current wave conducted through the water within probe 20 and is directed via connector 15 back through the function selector 44 to an amplifier 46. The returning wave is amplified by a known gain, which is adjustable by control knob 26 (FIG. 1) on the processing means 14 to calibrate the conductivity probe 12. The amplifier 46 output is directed through the function selector 44 to a precision rectifier and divide circuit 48, which reads the peak value of the clipped wave form received therein. This value is directed through an analog-to-digital converter and then to the display means 24 of the processing means 14. The display means 24 may be in the form of conventional alpha-numeric LCD displays. In the form of the invention illustrated, the spacing of the pairs of electrodes (35,37 and 37,39) is critical. As an example, electrode 39 (preferably an anode) is located within the sampling portion 20 of the conductivity probe 12 five cm (as shown by 54 on FIG. 3A) from common electrode 37 (cathode) used in the conductivity measurement. The voltage is then measured across a known five cm gap 54, between the electrodes 37 and 39 and is directed through the function selector 44 to the rectifier and divide circuit 48. The rectifier and divide circuit 48 then divides the voltage by five to get a "voltage per cm" value of field strength. The rectified field strength is directed to the filter and analog-to-digital converter 50 and displayed on digital display 24.

In use of the meter of the invention and in order to gather fish electrically as a result of electrotaxis, a minimum current must be passed through the body of the fish. Since all fish have a certain body resistivity, current passing through a fish's body follows Ohm's Law relative to producing a given head-to-tail voltage across the fish. It is believed that for most fresh waters, voltage gradients in the range of from about 0.1 to about 1.5 volts/cm are most effective in inducing electrotaxis and most preferably from about 0.1 to about 0.5 volts/cm. Therefore, for a 30-cm fish, approximately 3 to 15 head-to-tail volts are needed to induce electrotaxis and stun the fish sufficiently for collection in nets.

The apparatus of the present invention can be utilized in a process involving the following steps: the field strength conductivity probe 12 is placed in the water and a conductivity measurement between electrodes (35,37) is taken; the electroshocker 34 is adjusted to the desired voltage in conjunction with the generator 36 and the voltage is applied to the body of water; the conductivity probe 12 is then utilized to measure the field strength of the electric field to ensure that it is within desired limits for collecting fish.

The apparatus of the present invention is constructed with a processing means 14 which measures actual not temperature compensated water conductivity. The processing means 14 is constructed to read from 18 to 1,800 micromhos, within a tolerance of plus or minus five percent. Because the relationship between conductivity and resistance is reciprocal, it is difficult to calibrate a single conductivity meter which is capable of accurately reading conductivity or resistance over the entire range of possible conditions encountered in aquatic environments. Therefore, it is desirable to provide the meter of the present invention with a range which is selected by programming the desired range into the data processing unit 14. For instance, a low range may be selected from 2 to 500 micromhos, a mid-range from 500 to 1,500 micromhos and a higher range from about 1,000 to 2,500 micromhos. The invention has determined that calibration of the meter is much more precise when divided into such ranges. Alternatively, a meter may be provided with multiple ranges, any one of which could be manually selected depending upon the conditions to be encountered.

The invention has determined that the meter of the present invention may be capable of measuring an electric field strength of from about 0,005 volts/cm to about 2.0 volts/cm. An extended range may be provided up to 20 volts/cm if necessary for measurements in extremely pure waters.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A portable, hand-held apparatus for measuring the conductivity of a body of water and for measuring the field strength of an electric field applied to the body of water in order to operate a separate electroshocker for initiating electrotaxis in fish, comprising:
   a. a conductivity probe formed to permit water flow therethrough, said probe having three electrodes;
   b. a first pair of electrodes mounted within said conductivity probe for measuring a known current applied to the water to indicate the conductivity of the water;
   c. a second pair of electrodes mounted within said conductivity probe for measuring a field strength of a voltage gradient applied to said body of water by the electroshocker, said second pair of electrodes having one electrode in common with the first pair of electrodes;
   d. processing means electrically connected to said first and second pairs of electrodes for applying a known current to said first pair of electrodes to measure water conductivity and for measuring a potential between said second pair of electrodes; and
   e. display means for displaying data from said processing means.

2. The apparatus as recited in claim 1 and wherein: said processing means includes means to generate an oscillating sine wave of one kilohertz and means to shape the sine wave to about 0.7 volts.

3. The apparatus as recited in claim 2 and wherein: said apparatus further comprises a function selector switch for permitting the conductivity probe to be switched between measurements of the conductivity of the water or field strength of an electric field applied by the electroshocker to the water.

4. The apparatus as recited in claim 1 and wherein: the display means is an alpha-numeric LCD readout.

5. The apparatus as recited in claim 1 and wherein: said first pair of electrodes are spaced one cm apart and said second pair of electrodes are spaced five cm apart.

6. The method as recited in claim 1, further comprising the step of utilizing a metal boat as a negative electrode when externally applying the second voltage to the body of water.

7. The apparatus as recited in claim 1 and wherein: the voltage gradient measured is in the range of from about 0.005 volts per cm to 2.0 volts per cm.

8. An apparatus as recited in claim 7 and wherein: the electroshocker rectifies an A.C. voltage to a pulsating D.C. voltage.

9. An apparatus for determining conductivity of a body of water and for determining the field strength of an electric field applied to said body of water, comprising:
 a. a conductivity probe open to the body of water to permit water flow therethrough, and having three electrodes therein;
 b. a first pair of said electrodes measuring a first voltage to indicate the conductivity of said water and a second pair of said electrodes measuring the field strength of a second voltage in said body of water, the first and second pair of electrodes having one of said electrodes in common; and
 c. means to convert conductivity measurements and field strength measurements to a display.

10. A portable hand-held apparatus for measuring the conductivity of body of water and for measuring the field strength of an electric field applied to the body of water in order to operate a separate electroshocker for initiating electrotaxis in fish, comprising:
 a. a conductivity probe having a handle, a tube portion, and a sampling portion, said sampling portion having three electrodes thereon;
 b. a first pair of electrodes mounted on the sampling portion of the probe for measuring a known current applied to the water to indicate the conductivity of the water;
 c. a second pair of electrodes mounted on the sampling portion measuring the field strength of a voltage gradient applied to said body of water by the electroshocker mounted on the pair of electrodes having one electrode in common with the first pair of electrodes;
 d. processing means, electrically connected to said first and second pairs of electrodes for applying a known current to said first pair of electrodes to measure water conductivity and for measuring the voltage gradient between said second pair of electrodes; and
 e. display means for displaying data from said processing means.

11. Apparatus for determining conductivity of a body of water comprising:
 a. a conductivity probe open to the body of water to permit water flow therethrough, and having a plurality of electrodes therein;
 b. a first pair of said electrodes measuring the conductivity of said water utilizing a first voltage and a second pair of said electrodes measuring the field strength of a second voltage applied to said body of water; and
 c. means to convert conductivity measurements and field strength measurements to a display.

12. The apparatus as recited in claim 11 and wherein: said processing means includes means to generate an oscillating sine wave of one kilohertz and means to shape the sine wave to about 0.7 volts.

13. The apparatus as recited in claim 11 and wherein: the conductivity range measured is from about 18 to 1800 micromhos.

14. The apparatus as recited in claim 11 and wherein: the voltage gradient measured is in the range of from about 0.005 volts per cm to 2.0 volts per cm.

15. The apparatus as recited in claim 11 and wherein: the conductivity measured is in a low range of from 2 to 500 micromhos, a mid-range of from 500 to 1500 micromhos, and a high range of from about 1000 to 2500 micromhos.

16. The apparatus as recited in claim 10 and wherein: the display means is an alpha-numeric LCD readout.

17. A portable hand-held apparatus for measuring the conductivity of body of water and for measuring the field strength of an electric field applied to the body of water in order to operate a separate electroshocker for initiating electrotaxis in fish, comprising:
 a. a conductivity probe having a handle, a tube portion, and a sampling portion; the tube portion and the sample portion in the form of a "T", said sampling portion having three electrodes thereon;
 b. a first pair of electrodes in the form of metal pins mounted on the sampling portion of the probe for measuring a known current applied to the water to indicate the conductivity of the water, having an electrode spacing of one centimeter;
 c. a second pair of electrodes in the form of metal pins mounted on the sampling portion measuring the field strength of a voltage gradient applied to said body of water by the electroshocker, electrodes having a spacing of five centimeters on the probe, said second pair of electrodes having one electrode in common with the first pair of electrodes;
 d. processing means, electrically connected to said first and second pairs of electrodes for applying a known current to said first pair of electrodes to measure water conductivity and for measuring the voltage gradient between said second pair of electrodes; and
 e. alpha-numeric LCD readout for displaying data from said processing means.

18. The apparatus as recited in claim 17 and wherein: the conductivity range measured is from about 18 to 1800 micromhos.

19. The apparatus as recited in claim 17 and wherein: the voltage gradient measured is in the range of from about 0.005 volts per cm to 2.0 volts per cm.

20. The apparatus as recited in claim 17 and wherein: the conductivity measured is in a low range of from 2 to 500 micromhos, a mid-range of from 500 to 1500 micromhos, and a high range of from about 1000 to 2500 micromhos.

* * * * *